United States Patent [19]
Andrean et al.

[11] Patent Number: 6,077,320
[45] Date of Patent: Jun. 20, 2000

[54] USE OF DIIMINOISOINDOLINE DERIVATIVES OR 3-AMINOISOINDOLONE DERIVATIVES FOR DYEING KERATIN FIBERS, AND DYE COMPOSITIONS CONTAINING THEM

[75] Inventors: Hervé Andrean, Paris; Alain Lagrange, Coupvray, both of France

[73] Assignee: L'Oréal, Paris, France

[21] Appl. No.: 08/988,951

[22] Filed: Dec. 11, 1997

[30] Foreign Application Priority Data

Dec. 12, 1996 [FR] France .................................. 96 15290

[51] Int. Cl.⁷ ...................................................... A61K 7/13
[52] U.S. Cl. ..................... 8/405; 8/404; 8/408; 8/409; 8/429; 8/690; 8/574; 8/602; 8/586; 8/611; 8/916
[58] Field of Search ................ 8/404, 405, 429, 8/690, 574, 602, 586, 611, 916, 408, 409

[56] References Cited

U.S. PATENT DOCUMENTS 2,739,155  3/1956  Rosch et al. ............................ 548/471
4,521,793  6/1985  Kabashima et al. .................... 503/201

FOREIGN PATENT DOCUMENTS

| 43 35 623 | 4/1995 | Germany . |
| 44 09 143 | 9/1995 | Germany . |
| 1 020 305 | 2/1966 | United Kingdom . |
| 1187667 | 4/1970 | United Kingdom . |
| 2 181 750 | 4/1987 | United Kingdom . |

OTHER PUBLICATIONS

Derwent Abstract of JP 57/210077 (Abstr. No. 83–13364K), 12–1982.

*Primary Examiner*—Alan Diamond
*Attorney, Agent, or Firm*—Finnegan, Henderson, Farabow, Garrett & Dunner, L.L.P.

[57] ABSTRACT

Diiminoisoindoline derivatives or 3-aminoisoindolone derivatives, or tautomeric forms thereof, used as oxidizing-agent-free dye precursors in dyeing keratin fibers, in particular human keratin fibers such as the hair, without an oxidizing agent, in the presence of compounds containing a primary or secondary amine function; dye compositions containing these compounds and to the dyeing devices and processes used.

27 Claims, No Drawings

USE OF DIIMINOISOINDOLINE DERIVATIVES OR 3-AMINOISOINDOLONE DERIVATIVES FOR DYEING KERATIN FIBERS, AND DYE COMPOSITIONS CONTAINING THEM

The present invention relates to the use of diiminoisoindoline derivatives or 3-aminoisoindolone derivatives or tautomeric forms thereof for dyeing keratin fibers, in particular for human keratin fibers such as the hair, to the dye compositions containing them and to the dyeing devices and processes using these compositions.

For dyeing keratin fibers, and in particular the hair, it is known to use direct dyes or colored substances which give the fiber a temporary or semi-permanent coloration, of low dyeing power, which is generally removed by washing or perspiration, or oxidation dyes (oxidation bases and couplers) which are compounds that are initially colorless or weakly colored and give rise, by the action of an oxidizing agent, to colored compounds by a process of oxidative condensation. Compared with direct dyeing, oxidation dyeing is permanent, powerful and withstands external agents (light, bad weather, washing, perspiration and rubbing).

The inventors have now discovered, surprisingly and unexpectedly, that diiminoisoindoline derivatives or 3-aminoisoindolone derivatives or tautomeric forms thereof of formula (I) defined below, which are colorless compounds, can dye keratin fibers in the absence of an oxidizing agent, by reaction with certain specific reactants, in particular compounds with a primary or secondary amine function.

This discovery forms the basis of the present invention.

The subject of the present invention is thus the use of diiminoisoindoline derivatives or 3-amino-isoindolone derivatives or tautomeric forms thereof of formula (I) defined below, for dyeing keratin fibers, in particular human keratin fibers such as the hair.

A subject of the invention is also the use of the abovementioned derivatives as oxidizing-agent-free dye precursors in, or for the preparation of, compositions for dyeing keratin fibers, in particular human keratin fibers such as the hair.

The expression "oxidizing-agent-free dye precursor" is understood to refer to a compound which is essentially colorless and is capable of giving rise to a coloration without the addition of an oxidizing agent, by reaction with another compound that reacts with it.

A subject of the present invention is also the use of the abovementioned derivatives as oxidizing-agent-free dye precursors, in combination with a compound containing a primary or secondary amine function, in compositions for dyeing keratin fibers, in particular human keratin fibers such as the hair.

The invention also relates to compositions for dyeing keratin fibers, in particular human keratin fibers such as the hair, containing, in a medium which is suitable for dyeing, at least one diiminoisoindoline derivative or 3-aminoisoindolone derivative or the tautomeric form thereof of formula (I) defined below, as oxidizing-agent-free dye precursor.

The invention also relates to compositions for dyeing keratin fibers, in particular human keratin fibers such as the hair, containing, in a medium which is suitable for dyeing, (i) at least one diiminoiso-indoline derivative or 3-aminoisoindolone derivative, or the tautomeric form thereof of formula (I) defined below, and (ii) a compound containing a primary or secondary amine function.

Another subject of the invention is a two-component composition for which, in a medium which is suitable for dyeing, one component contains at least one diiminoisoindoline derivative or 3-aminoisoindolone derivative, or the tautomeric form thereof of formula (I) defined below, and the other contains a compound containing a primary or secondary amine function, and which, stored separately, are (i) mixed together, at the time of use, for application to the keratin fibers, or (ii) applied sequentially to the fibers.

A subject of the invention is also the dyeing processes using these compositions.

Another subject of the invention relates to a multi-compartment device, or "kit", for dyeing keratin fibers, characterized in that it contains at least two compartments, one of which holds a composition containing, in a medium which is suitable for dyeing, at least one diiminoisoindoline derivative or 3-aminoisoindolone derivative, or the tautomeric form thereof of formula (I) defined below, and the other holds a composition containing, in a medium which is suitable for dyeing, a compound capable of reacting, without an oxidizing agent, with the compound of formula (I) in order to form a dye.

The invention also relates to a multi-compartment device, or "kit", for dyeing keratin fibers, characterized in that it contains at least two compartments, one of which holds a composition containing, in a medium which is suitable for dyeing, at least one diiminoisoindoline derivative or 3-amino-isoindolone derivative, or the tautomeric form thereof of formula (I) defined below, and the other holds a composition containing, in a medium which is suitable for dyeing, a composition containing a primary or secondary amine function.

The dyes obtained with the compositions according to the invention are powerful and withstand external agents (light, bad weather, washing, perspiration and rubbing).

However, other characteristics, aspects and advantages of the invention will become even more apparent on reading the description which follows, as well as the various concrete, but in no way limiting, examples intended to illustrate it.

The diiminoisoindoline derivatives or 3-aminoisoindolone derivatives, or the tautomeric forms thereof, are compounds of formula (I) below:

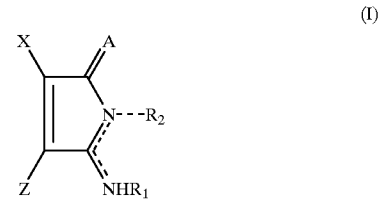

in which

R$_1$ and R$_2$ denote, independently of each other, hydrogen, alkyl, hydroxyalkyl, polyhydroxyalkyl, alkylhydroxyalkyl, aminoalkyl (it being possible for the amine to be protected with an acetyl, ureido or sulphonyl radical), alkylaminoalkyl, (dihydroxy)alkylaminoalkyl or -alkyl-NR'R" (in which R' and R" are alkyl or can form, together with the nitrogen atom to which they are attached, a 5- or 6-membered aliphatic or heterocyclic ring), it being understood that all the alkyl radicals of the groups defined above contain from 1 to 4 carbon atoms and may be linear or branched, and further wherein R$_2$ optionally is not present, A denotes O or NH, X and Z together form a saturated or unsaturated, aromatic or heterocyclic, 5- or 6-membered hydrocarbon ring which may be interrupted by one or more nitrogen or sulphur atoms, and which can be substituted with one or more radicals such as $NO_2$, $NH_2$, acetylamino, OH, $SO_3H$, halogen (Br, Cl, F), $CH_3SO_2$, $-CF_3$, $-OCF_3$, $C_1-C_4$alkyl, $(C_1-C_4)$alkoxy, $(C_1-C_4)$alkylthio, $(C_1-C_4)$alkoxycarbonyl, and the cosmetically acceptable salts of these compounds.

Such compounds are known per se, have been prepared in the prior art, and are, in particular, the following:

3-imino-3H-isoindol-1-ylamine,
3-imino-4-methyl-3H-isoindol-1-ylamine,
3-imino-4-tert-butyl-3H-isoindol-1-ylamine,
3-imino-7-nitro-3H-isoindol-1-ylamine,
3-amino-1-imino-1H-isoindol-4-ol,
3-imino-7-isopropoxy-3H-isoindol-1-ylamine,
3-imino-7-(2,2,2-trifluoroethoxy)-3H-isoindol-1-ylamine,
3-imino-7-ethoxy-3H-isoindol-1-ylamine,
3-imino-7-butoxy-3H-isoindol-1-ylamine,
3-amino-1-imino-1H-isoindole-4-sulphonic acid
3-imino-7-chloro-3H-isoindol-1-ylamine,
3-imino-5-methyl-3H-isoindol-1-ylamine,
3-imino-5-ethyl-3H-isoindol-1-ylamine,
3-imino-5-tertbutyl-3H-isoindol-1-ylamine,
3-imino-5-amino-3H-isoindol-1-ylamine,
N-(1-amino-3-imino-3H-isoindol-5-yl)acetamide,
3-imino-5-nitro-3H-isoindol-1-ylamine,
3-imino-5-fluoro-3H-isoindol-1-ylamine,
3-imino-5-chloro-3H-isoindol-1-ylamine,
3-imino-5-methylsulphanyl-3H-isoindol-1-ylamine,
3-imino-5-methoxy-3H-isoindol-1-ylamine,
3-imino-5-ethoxy-3H-isoindol-1-ylamine,
3-imino-5-propoxy-3H-isoindol-1-ylamine,
3-imino-5-butoxy-3H-isoindol-1-ylamine,
3-imino-5-isobutoxy-3H-isoindol-1-ylamine,
3-imino-5-tert-butoxy-3H-isoindol-1-ylamine,
3-imino-5-(2,2,2-trifluoromethyl)-3H-isoindol-1-ylamine,
3-imino-5-(2,2,2-trifluoroethoxy)-3H-isoindol-1-ylamine,
3-imino-5-methanesulphonyl-3H-isoindol-1-ylamine,
3-imino-5,6-dimethyl-3H-isoindol-1-ylamine,
3-imino-5,6-diethyl-3H-isoindol-1-ylamine,
3-imino-5,6-dimethoxy-3H-isoindol-1-ylamine,
3-imino-5,6-diethoxy-3H-isoindol-1-ylamine,
3-imino-5,6-dibutoxy-3H-isoindol-1-ylamine,
3-imino-5,6-bis(trifluoromethyl)-3H-isoindol-1-ylamine,
3-imino-5,6-dichloro-3H-isoindol-1-ylamine,
5,6-bis(ethoxymethyl)-3-imino-3H-isoindol-1-ylamine,
3-amino-1-imino-1H-isoindole-4,7-diol,
4,7-dichloro-3-imino-3H-isoindol-1-ylamine,
4,5,7-trichloro-3-imino-N6,N6-dimethyl-3H-isoindole-1,6-diamine,
4,5,6,7-tetrachloro-3-imino-3H-isoindol-1-ylamine,
4,5,6,7-tetrafluoro-3-imino-3H-isoindol-1-ylamine,
2-(3-aminoisoindol-1-ylideneamino)ethanol,
3-(3-aminoisoindol-1-ylideneamino)-3-methylpentane-1,5-diol,
N-(3-aminoisoindol-1-ylidene)guanidine,
7-imino-7H-pyrrolo[3,4-b]pyrid-5-ylamine,
7-imino-7H-pyrrolo[3,4-b]pyrazin-5-ylamine,
7-imino-2,3-dimethyl-7H-pyrrolo[3,4-b]pyrazin-5-ylamine,
7-imino-7H[1,4]dithiino[2,3-c]pyrrol-5-ylamine,
7-imino-2,3-dimethyl-7H-[1,4]dithiino[2,3-c]pyrrol-5-ylamine,
7-imino-2,3-dihydro-7H-[1,4]dithiino[2,3-c]pyrrol-5-ylamine,
7-imino-2-methyl-2,3-dihydro-7H-[1,4]dithiino[2,3-c]pyrrol-5-ylamine,
3-aminoisoindol-1-one,
3-amino-7-methylisoindol-1-one,
3-amino-7-hydroxymethylisoindol-1-one,
3-amino-7-chloroisoindol-1-one,
3-amino-4-chloroisoindol-1-one,
3-amino-1-oxo-1H-isoindole-4-sulphonic acid,
3-amino-4-nitroisoindol-1-one,
3-amino-6-nitroisoindol-1-one,
3-amino-6-methylisoindol-1-one,
3-amino-6-chloroisoindol-1-one,
3-amino-6-bromoisoindol-1-one,
3-amino-6-methylsulphanylisoindol-1-one,
3-amino-6-methoxyisoindol-1-one,
3-amino-5-chloroisoindol-1-one,
3-amino-5-fluoroisoindol-1-one,
3-amino-5-methoxyisoindol-1-one,
3-amino-5-nitroisoindol-1-one,
ethyl 3-amino-1-oxo-1H-isoindole-5-carboxylate
3-amino-5,6-dichloroisoindol-1-one,
3-amino-5,6-dibromoisoindol-1-one,
3-amino-4,7-dichloroisoindol-1-one,
3-amino-4,5,7-trichloroisoindol-1-one,
3-amino-4,5,6,7-tetrachloroisoindol-1-one,
3-amino-4,5,7-trichloro-6-methylsulphanylisoindol-1-one,
3-amino-4,5,6,7-tetrabromoisoindol-1-one,
3-amino-4,5,6,7-tetrafluoroisoindol-1-one,
3-methylaminoisoindol-1-one,
3-ethylaminoisoindol-1-one,
3-propylaminoisoindol-1-one,
3-dimethylaminoisoindol-1-one,
7-ethylaminopyrrolo[3,4-b]pyrid-5-one,
7-aminopyrrolo[3,4-b]pyrid-5-one,
3-aminopyrrolo[3,4-c]pyrid-5-one,
3-amino-6-methylpyrrolo[3,4-c]pyrid-1-one,
5-aminopyrrolo[3,4-b]pyrid-7-one,
7-aminopyrrolo[3,4-b]pyrazin-5-one,
7-amino-2-methylpyrrolo[3,4-b]pyrazin-5-one,
7-amino-2,3-dimethylpyrrolo[3,4-b]pyrazin-5-one,
7-amino-2,3-dihydro-[1,4]dithiino[2,3-c]pyrrol-5-one,
3-imino-2-methyl-2,3-dihydroisoindol-1-one,
3-imino-2-ethyl-2,3-dihydroisoindol-1-one,
3-imino-2-propyl-2,3-dihydroisoindol-1-one,
2-hydroxymethyl-3-imino-2,3-dihydroisoindol-1-one,
2-(2-hydroxyethyl)-3-imino-2,3-dihydroisoindol-1-one,
2-(1-imino-3-oxo-1,3-dihydroisoindol-2-yl)ethanesulphonic acid,
3-(1-imino-3-oxo-1,3-dihydroisoindol-2-yl)propionic acid,
2-(3-hydroxypropyl)-3-imino-2,3-dihydroisoindol-1-one,
5-imino-6-methyl-5,6-dihydropyrrolo[3,4-b]pyrid-7-one,
and the cosmetically acceptable salts thereof.

Among the compounds containing a primary or secondary amine function which can be used in the dye compositions according to the present invention, mention may be made in particular of:

aromatic amines such as N,N-bis(2-hydroxyethyl)-p-phenylenediamine, 2-(2-hydroxyethyl)-p-phenylenediamine, N-(2-hydroxyethyl)-N-ethyl-p-phenylenediamine, N-(2-methoxyethyl)-p-phenylenediamine, 2-chloro-p-phenylenediamine, 2-, 3- and 4-amino-phenols, o-, m- and p-phenylenediamines, 2,5-diaminotoluene, 2,5-diaminophenol, 2,5-diaminoanisole, 4-methylaminoaniline, 3,4-dimethyl-aminoaniline, 3,4-methylenedioxyaniline, 3-amino-2,4-dichlorophenol, 4-methylaminophenol, 2-methyl-5- aminophenol, 3-methyl-4-aminophenol, 2-methyl-5-amino-6-chlorophenol, 2-methyl-5-amino-4-chlorophenol, 1,3-diamino-2,4-dimethoxybenzene, 2-, 3-, and 4-aminobenzoic acid, 2-, 3- and 4-aminophenylacetic acids, 2,3-, 2,4-, 2,5-, 3,4- and 3,5-diaminobenzoic acids, 4- and 5-aminosalicyclic acids, 3-amino-4-hydroxybenzoic acid, 4-amino-3-hydroxybenzoic acid, 2-, 3- and 4-aminobenzenesulphonic acid, 3-amino-4-hydroxybenzenesulphonic acid, 4-amino-3-hydroxy-naphthalene-1-sulphonic acid, 7-amino-4-hydroxy-naphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5- and 1,2,4-triaminobenzene, 1,2,4,5-tetraaminobenzene, 2,4,5-triaminophenol, pentaaminobenzene, hexaaminobenzene, 2,4,6-triamino-resorcin, 4,5-diaminopyrocatechol, 4,6-diamino-pyrogallol, 3,5-diamino-4-hydroxypyrocatechol, 2-methyl-5-(2-hydroxyethylamino)phenol, 2-methoxy-3,5-dimethyl-4-aminobenzene, 2,6-dimethyl-4-bis(2-hydroxyethyl)amino-1-aminobenzene, 5,6-dimethoxy-1,3-diaminobenzene, 2,6-dimethyl-1,3-diaminobenzene, 2,6-dimethoxy-5-chloro-1,3-diaminobenzene, 2,6-dimethoxy-3-(2-hydroxyethyl)amino-1-aminobenzene, 2,4-dimethoxy-3-(2-hydroxyethyl)amino-1-aminobenzene, 4,6-dibenzyloxy-1,3-diaminobenzene, 3-methyl-6-methoxy-1,2-diaminobenzene, 3,5-dimethyl-4-aminophenol, 2,5-dimethyl-4-aminophenol, 2,3,5-trimethyl-4-aminophenol, 2,3,5,6-tetramethyl-4-aminophenol, 4-chloro-5-acetylamino-2-aminophenol, 4,6-diphenyloxy-1,3-diaminobenzene, 2,6-dimethyl-1,4-diaminobenzene, 2,5-dimethyl-4-aminobenzene, 2,3-dimethyl-4-aminobenzene, 2-methoxy-5-methyl-1,4-diaminobenzene, 2-methoxy-5-methyl-4-(2-aminoethyl)amino-1-aminobenzene, 2-methyl-5-chloro-4-(2-aminoethyl)amino-1-aminobenzene, 4,6-dimethoxy-1,3-diaminobenzene, 2,3-dimethyl-4-aminophenol, 2,6-dimethyl-4-aminophenol, 2,5-dimethyl-3-aminophenol, N,N'-bis(2-hydroxyethyl)-N,N'-bis(4-aminophenyl)-1,3-diamino-2-propanol, N,N'-bis(2-hydroxyethyl)-N,N'-bis(4-aminophenyl)ethylenediamine, N,N'-bis(4-aminophenyl)tetramethylenediamine, N,N'-bis(2-hydroxyethyl)-N,N'-bis(4-aminophenyl)tetramethylene-diamine and N,N'-bis(ethyl)-N,N'-bis(4-amino-3-methylphenyl)ethylenediamine, and the cosmetically acceptable salts thereof, and heterocyclic amines such as 2-, 3- and 4-aminopyridine, 2-amino-3-hydroxypyridine, 2,3-, 2,5-, 2,6- and 3,4-diaminopyridine, 2-dimethylamino-5-aminopyridine, 3-amino-2-methylamino-6-methoxypyridine, 2,3-diamino-6-methoxypyridine, 2,4,5- and 4,5,6-triaminopyrimidine, 2,6-dimethoxy-3,5-diaminopyridine, 6-methoxy-2,3-diaminopyridine, 4-hydroxy-2,5,6-triaminopyrimidine, 2,4,5,6-tetraaminopyrimidine, 2-methylamino-4,5,6-triaminopyrimidine, 2,4- and 4,5-diaminopyrimidine, 2-amino-4-methoxy-6-methylpyrimidine, 5,6-diamino-2,4-dihydroxypyrimidine, 3,4-diaminothiophene, 3,5-diaminopyrazole, 1-methyl-4,5-diaminopyrazole, 1-ethyl-4,5-diaminopyrazole, 1,3-dimethyl-4,5-diaminopyrazole, 1-ethyl-3-methyl-4,5-diaminopyrazole, 1-(4'-chlorobenzyl)-4,5-diaminopyrazole, 3-aminopyrazoline, 1H-1,2,4-triazole, 3-aminopyrazole, 3-amino-5-hydroxypyrazole, 2-, 3- and 8-aminoquinoline, 5-aminoisoquinoline, 2- and 6-aminonicotinic acid, 4-, 5-, 6- and 7-aminoindole, 2,3-dimethyl-5-amino-6-hydroxyindole, 2,3-dimethyl-5-amino-6-methoxyindole, 2,3-dimethyl-5-chloro-6-aminoindole, 2,3,4,5-tetramethyl-6-aminoindole, 2,3-dimethyl-5-methoxy-6-aminoindole, 2,3-dimethyl-5-ethyl-6-aminoindole, 2-methyl-6-aminoindole, 2,3-dimethyl-5-hydroxy-6-aminoindole, 2,3,5-trimethyl-6-aminoindole, 2-methyl-5-hydroxy-6-aminoindole, 2,3-dimethyl-6-aminoindole, 2,3,7-trimethyl-6-aminoindole, 2,3,4-trimethyl-6-aminoindole, 5- and 6-aminoindazole, 5- and 7-aminobenzimidazole, 5- and 7-aminobenzothiazole, 2,5-dihydroxy-4-morpholino-aniline, 5,6-dihydroxyindoline, 4-hydroxyindole, 6-aminoindoline, N-ethyl-6-aminoindoline, 3-, 4-, 5-, 6- and 7-aminoindazoles, 1-methyl 3-, 4-, 5-, 6- and 7-aminoindazole, 2-methyl 3-, 4-, 5-, 6- and 7-aminoindazoles, pyrazolo[1,5-a]pyrimidine-6,7-diamine, 5,6-dimethylpyrazolo[1,5-a]-pyrimidine-3,7-diamine, 2,6-dimethylpyrazolo[1,5-a]pyrimidine-3,7-diamine, 2,5-N7,N7-tetra-methylpyrazolo[1,5-a]pyrimidine-3,7-diamine, 2,3-dimethylpyrazolo[1,5-a]pyrimidine-6,7-diamine, 6-amino-5-methylpyrazolo[1,5-a]pyrimidin-7-ol, pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-amino-pyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo-[1,5-a]pyrimidin-7-yl)-(2-hydroxyethyl)amino]ethanol and 2-[(7-aminopyrazolo[1,5-a]pyrimidin-3-yl)-(2-hydroxyethyl)amino]ethanol, and the cosmetically acceptable salts thereof, and amino acids or oligopeptides containing from 2 to 9 amino acids, of natural or synthetic origin and obtained by hydrolysis of plant proteins or animal proteins such as, for example, collagen, keratin, casein, elastin, soya protein, wheat gluten or almond protein. The preferred amino acids are tyrosine, histidine, lysine, phenylalanine, ornithine, dopa, arginine and tryptophan.

For the purposes of the present invention, the cosmetically acceptable salts of the compounds of formula (I) and of the abovementioned amines can be hydrochlorides, sulphates, hydrobromides or tartrates.

The concentration of compound of formula (I) preferably ranges from approximately 0.01 to approximately 5%, and even more preferably from approximately 0.15 to approximately 2% by weight, relative to the total weight of the dye composition.

The concentration of compound containing a primary or secondary amine function preferably ranges from approximately 0.01 to approximately 5%, and even more preferably from approximately 0.15 to approximately 2% by weight, relative to the total weight of the dye composition.

The medium which is suitable for dyeing is preferably an aqueous medium consisting of water and/or cosmetically acceptable organic solvents, and more particularly alcohols such as ethyl alcohol, isopropyl alcohol, benzyl alcohol and phenylethyl alcohol, or glycols or glycol ethers such as, for example, ethylene glycol and the monomethyl, monoethyl and monobutyl ethers thereof, propylene glycol or the ethers thereof such as, for example, propylene glycol monomethyl ether, butylene glycol, dipropylene glycol and diethylene glycol alkyl ethers such as, for example, diethylene glycol monoethyl ether or monobutyl ether, in concentrations preferably ranging from approximately 0.5 to approximately 20%, and more preferably from approximately 2 to approximately 10%, by weight relative to the total weight of the composition.

Fatty amides such as mono- and diethanolamides of coconut-derived acids, of lauric acid or of oleic acid can also be added to the composition according to the invention, in concentrations preferably ranging from approximately 0.05 to approximately 10% by weight.

Surfactants that are well known in the prior art and of anionic, cationic, nonionic, amphoteric or zwitterionic type or mixtures thereof can also be added to the composition according to the invention, preferably in a proportion of approximately 0.1 to approximately 50% by weight and more preferably of approximately 1 to approximately 20% by weight, relative to the total weight of the composition.

Thickeners can also be used in a proportion preferably ranging from approximately 0.2 to approximately 20%.

The dye composition can also contain various common adjuvants such as antioxidants, fragrances, sequestering agents, dispersing agents, hair conditioners, preserving agents and opacifiers, as well as any other adjuvant usually used to dye keratin fibers.

Needless to say, a person skilled in the art will take care to select the optional complementary compound(s) mentioned above, such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to range, for example, from 2 to 11 and preferably from 5 to 10, and it being possible for it to be adjusted using basifying agents or acidifying agents or buffers that are well known previously.

As basifying agents, mention may be made of aqueous ammonia, alkaline carbonates, alkanolamines, for example mono-, di- and triethanolamine and derivatives thereof, sodium hydroxide, potassium hydroxide and the compounds of formula:

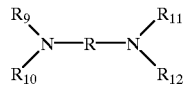

in which R is a propylene residue optionally substituted with a hydroxyl group or a $C_1$–$C_4$ alkyl radical; $R_9$, $R_{10}$, $R_{11}$ and $R_{12}$, simultaneously or independently of each other, represent a hydrogen atom or a $C_1$–$C_4$ alkyl or $C_1$–$C_4$ hydroxyalkyl radical.

The acidifying agents are conventionally inorganic or organic acids such as, for example, hydrochloric acid, tartaric acid, citric acid and phosphoric acid. Among the buffers, mention may be made, for example, of potassium dihydrogen phosphate/sodium hydroxide.

The composition applied to the hair can be in various forms, such as in liquid, cream or gel form or in any other form which is suitable for dyeing keratin fibers. In particular, it can be packaged under pressure in an aerosol can in the presence of a propellant and form a foam.

Another subject of the present invention relates to a process for dyeing keratin substances, in particular human keratin fibers such as the hair, this process involving applying a dye composition comprising, in a medium which is suitable for dyeing, at least one diiminoisoindoline derivative or 3-aminoisoindolone derivative, or the tautomeric form thereof of formula (I), and a compound containing a primary or secondary amine function, on wet or dry keratin fibers, in leaving the composition to act on the fibers for an exposure time preferably ranging from approximately 3 to approximately 60 minutes, and more preferably from approximately 5 to approximately 45 minutes, in rinsing, optionally washing, then rinsing again and drying the fibers.

A process variant constitutes another subject of the invention and consists in applying to the keratin fibers, simultaneously or sequentially (i) a dye composition comprising, in a medium which is suitable for dyeing, at least one diiminoisoindoline derivative or 3-aminoisoindolone derivative, or the tautomeric form thereof of formula (I), and (ii) a composition essentially holding a compound containing a primary or secondary amine function in a medium which is suitable for dyeing.

Concrete examples illustrating the invention, but in no way limiting the invention, will now be given.

EXAMPLE 1

| The following dye composition was prepared, just before use: | |
|---|---|
| 3-imino-3H-isoindol-1-ylamine | 0.435 g |
| 2-(2-hydroxyethyl)-p-phenylenediamine HCl | 0.675 g |
| benzyl alcohol | 10.0 g |
| 50/50 cetyl/stearyl alcohol | 8.9 g |
| sodium cetyl stearyl sulphate | 8.9 g |
| water | qs 100 g |

The above composition was applied to locks of natural grey hair containing 90% white hairs and was left in place for 30 minutes. After rinsing with running water and drying, the hair was dyed an orange shade.

EXAMPLE 2

| The following dye composition was prepared, just before use: | |
|---|---|
| 3-aminoisoindol-1-one | 0.438 g |
| 2-(2-hydroxyethyl)-p-phenylenediamine HCl | 0.675 g |
| benzyl alcohol | 10.0 g |
| 50/50 cetyl/stearyl alcohol | 8.9 g |
| sodium cetyl stearyl sulphate | 8.9 g |
| water | qs 100 g |

The above composition was applied to locks of natural grey hair containing 90% white hairs and was left in place for 30 minutes. After rinsing with running water and drying, the hair was dyed a yellow shade.

EXAMPLE 3

| The following dye composition was prepared, just before use: | |
|---|---|
| 3-imino-3H-isoindol-1-ylamine | 0.435 g |
| N,N-bis(2-hydroxyethyl)-p-phenylene diamine sulphate sulphate | 0.588 g |
| benzyl alcohol | 10.0 g |
| 50/50 cetyl/stearyl alcohol | 8.9 g |

-continued

| The following dye composition was prepared, just before use: | |
|---|---|
| sodium cetyl stearyl sulphate | 8.9 g |
| water | qs 100 g |

The above composition was applied to locks of permanent-waved grey hair containing 90% white hairs and was left in place for 30 minutes. After rinsing with running water and drying, the hair was dyed a rosewood shade.

EXAMPLE 4

| The following dye composition was prepared, just before use: | |
|---|---|
| 3-aminoisoindol-1-one | 0.438 g |
| N,N-bis(2-hydroxyethyl)-p-phenylene diamine sulphate sulphate | 0.588 g |
| benzyl alcohol | 10.0 g |
| 50/50 cetyl/stearyl alcohol | 8.9 g |
| sodium cetyl stearyl sulphate | 8.9 g |
| water | qs 100 g |

The above composition was applied to locks of permanent-waved grey hair containing 90% white hairs and was left in place for 30 minutes. After rinsing with running water and drying, the hair was dyed a greyish straw-yellow shade.

EXAMPLE 5

| The following dye composition was prepared, just before use: | |
|---|---|
| 3-imino-3H-isoindol-1-ylamine | 0.435 g |
| 2,6-diaminopyridine 2HCl | 0.546 g |
| ethyl alcohol | 30.0 g |
| water | qs 100 g |

The above composition was applied to locks of natural grey hair containing 90% white hairs and was left in place for 30 minutes. After rinsing with running water and drying, the hair was dyed a straw-yellow shade.

EXAMPLE 6

| The following dye composition was prepared, just before use: | |
|---|---|
| 3-imino-3H-isoindol-1-ylamine | 0.435 g |
| 3,7-diaminopyrazolo[1,5-a]pyrimidine 2HCl | 0.666 g |
| ethyl alcohol | 30.0 g |
| water | qs 100 g |

The above composition was applied to locks of natural grey hair containing 90% white hairs and was left in place for 30 minutes. After rinsing with running water and drying, the hair was dyed an orange-yellow shade.

EXAMPLE 7

| The following dye composition was prepared, just before use: | |
|---|---|
| 3-imino-3H-isoindol-1-ylamine | 0.435 g |
| 3-aminopyrazoline 2HCl | 0.747 g |
| ethyl alcohol | 30.0 g |
| water | qs 100 g |

The above composition was applied to locks of permanent-waved grey hair containing 90% white hairs and was left in place for 30 minutes. After rinsing with running water and drying, the hair was dyed a grey-green shade.

EXAMPLE 8

| The following dye composition was prepared, just before use: | |
|---|---|
| 3-imino-3H-isoindol-1-ylamine | 0.435 g |
| 1-(4'-chlorobenzyl)-4,5-diamino-pyrazole 2HCl | 0.886 g |
| ethyl alcohol | 30.0 g |
| water | qs 100 g |

The above composition was applied to locks of permanent-waved grey hair containing 90% white hairs and was left in place for 30 minutes. After rinsing with running water and drying, the hair was dyed an orange shade.

EXAMPLE 9

| The following dye composition was prepared, just before use: | |
|---|---|
| 3-imino-3H-isoindol-1-ylamine | 0.435 g |
| 5-aminoindole | 0.396 g |
| ethyl alcohol | 30.0 g |
| water | qs 100 g |

The above composition was applied to locks of grey hair containing 90% white hairs and was left in place for 30 minutes. After rinsing with running water and drying, the hair was dyed a yellow-orange shade.

EXAMPLE 10

| The following dye composition was prepared, just before use: | |
|---|---|
| 3-imino-3H-isoindol-1-ylamine | 0.435 g |
| 2-methyl-7-aminoindazole HCl | 0.551 g |
| ethyl alcohol | 30.0 g |
| water | qs 100 g |

The above composition was applied to locks of permanent-waved grey hair containing 90% white hairs and was left in place for 30 minutes. After rinsing with running water and drying, the hair was dyed a pale yellow shade.

EXAMPLE 11

| The following dye composition was prepared, just before use: | |
|---|---|
| 3-imino-3H-isoindol-1-ylamine | 0.435 g |
| 3,4-diaminothiophene 2HBr | 0.828 g |
| ethyl alcohol | 30.0 g |
| water | qs 100 g |

The above composition was applied to locks of grey hair containing 90% white hairs and was left in place for 30 minutes. After rinsing with running water and drying, the hair was dyed a bronze-green shade.

EXAMPLE 12

| The following dye composition was prepared, just before use: | |
|---|---|
| 3-imino-3H-isoindol-1-ylamine | 0.435 g |
| 1,3-dimethyl-4,5-diaminopyrazole 2HCl | 0.597 g |
| ethyl alcohol | 30.0 g |
| water | qs 100 g |

The above composition was applied to locks of grey hair containing 90% white hairs and was left in place for 30 minutes. After rinsing with running water and drying, the hair was dyed an orange-yellow shade.

EXAMPLE 13

| The following dye composition was prepared, just before use: | |
|---|---|
| 3-imino-3H-isoindol-1-ylamine | 0.435 g |
| 1-methyl-4,5-diaminopyrazole 2HCl | 0.555 g |
| ethyl alcohol | 30.0 g |
| water | qs 100 g |

The above composition was applied to locks of permanent-waved grey hair containing 90% white hairs and was left in place for 30 minutes. After rinsing with running water and drying, the hair was dyed a bright orange shade.

EXAMPLE 14

| The following dye composition was prepared, just before use: | |
|---|---|
| 3-imino-3H-isoindol-1-ylamine | 0.435 g |
| 3-methyl-4-aminophenol HBr | 0.612 g |
| ethyl alcohol | 30.0 g |
| water | qs 100 g |

The above composition was applied to locks of permanent-waved grey hair containing 90% white hairs and was left in place for 30 minutes. After rinsing with running water and drying, the hair was dyed a yellow shade.

EXAMPLE 15

| The following dye composition was prepared, just before use: | |
|---|---|
| 3-imino-3H-isoindol-1-ylamine | 0.435 g |
| 4-aminoindazole 2HCl | 0.618 g |
| ethyl alcohol | 30.0 g |
| water | qs 100 g |

The above composition was applied to locks of permanent-waved grey hair containing 90% white hairs and was left in place for 30 minutes. After rinsing with running water and drying, the hair was dyed a pink-beige shade.

We claim:

1. A method for dyeing a keratin fiber, said method comprising applying to said keratin fiber a compound of formula (I) or a cosmetically acceptable salt thereof:

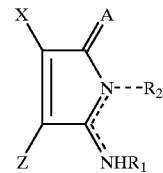

(I)

in which $R_1$ and $R_2$, which are the same or different, denote hydrogen, alkyl, hydroxyalkyl, polyhydroxyalkyl, alkylhydroxyalkyl, aminoalkyl, alkylaminoalkyl, (dihydroxy)alkylaminoalkyl, or -alkyl-NR'R" wherein R' and R" are alkyl or form, together with the nitrogen atom to which they are attached, a 5- or 6-membered aliphatic or heterocyclic ring;

wherein all the alkyl groups of $R_1$, $R_2$, R' and R" contain from 1 to 4 carbon atoms and are linear or branched, and further wherein $R_2$ optionally is not present, A denotes O or NH;

X and Z together form a saturated or unsaturated, aromatic or heterocyclic, 5- or 6-membered hydrocarbon ring which is optionally interrupted by one or more nitrogen or sulphur atoms, and which is optionally substituted with one or more groups comprising $NO_2$, $NH_2$, acetylamino, OH, $SO_3H$, F, Cl, Br, $CH_3SO_2$, $-CF_3$, $-OCF_3$, $(C_1-C_4)$alkoxy, $(C_1-C_4)$alkylthio, and $(C_1-C_4)$alkoxycarbonyl.

2. A method according to claim 1, wherein when $R_1$ and/or $R_2$ is an aminoalkyl, and said aminoalkyl is protected with an acetyl, ureido or sulphonyl radical.

3. A method according to claim 1, wherein said keratin fiber is human hair.

4. A method according to claim 1, wherein said compound of formula (I) is selected from:
3-imino-3H-isoindol-1-ylamine,
3-imino-4-methyl-3H-isoindol-1-ylamine,
3-imino-4-tertbutyl-3H-isoindol-1-ylamine,
3-imino-7-nitro-3H-isoindol-1-ylamine,
3-imino-1-imino-1H-isoindol-4-ol,
3-imino-7-isopropoxy-3H-isoindol-1-ylamine,
3-imino-7-(2,2,2-trifluoroethoxy)-3H-isoindol-1-ylamine,
3-imino-7-ethoxy-3H-isoindol-1-ylamine,
3-imino-7-butoxy-3H-isoindol-1-ylamine,
3-imino-1-imino-1H-isoindole-4-sulphonic acid,
3-imino-7-chloro-3H-isoindol-1-ylamine, 3-imino-5-methyl-3H-isoindol-1-ylamine,
3-imino-5-ethyl-3H-isoindol-1-ylamine,
3-imino-5-tertbutyl-3H-isoindol-1-ylamine,
3-imino-5-amino-3H-isoindol-1-ylamine,
N-(1-amino-3-imino-3H-isoindol-5-yl)acetamide,
3-imino-5-nitro-3H-isoindol-1-ylamine,
3-imino-5-fluoro-3H-isoindol-1-ylamine,
3-imino-5-chloro-3H-isoindol-1-ylamine,
3-imino-5-methylsulphanyl-3H-isoindol-1-ylamine,
3-imino-5-methoxy-3H-isoindol-1-ylamine,
3-imino-5-ethoxy-3H-isoindol-1-ylamine,
3-imino-5-propoxy-3H-isoindol-1-ylamine,
3-imino-5-isopropoxy-3H-isoindol-1-ylamine,
3-imino-5-butoxy-3H-isoindol-1-ylamine,
3-imino-5-isobutoxy-3H-isoindol-1-ylamine,
3-imino-5-tertbutoxy-3H-isoindol-1-ylamine,
3-imino-5-(2,2,2-trifluoromethyl)-3H-isoindol-1-ylamine,
3-imino-5-(2,2,2-trifluoroethoxy)-3H-isoindol-1-ylamine,
3-imino-5-methanesulphonyl-3H-isoindol-1-ylamine,
3-imino-5,6-dimethyl-3H-isoindol-1-ylamine,
3-imino-5,6-diethyl-3H-isoindol-1-ylamine,
3-imino-5,6-dimethoxy-3H-isoindol-1-ylamine,
3-imino-5,6-diethoxy-3H-isoindol-1-ylamine,
3-imino-5,6-dibutoxy-3H-isoindol-1-ylamine,
3-imino-5,6-bis(trifluoromethyl)-3H-isoindol-1-ylamine,
3-imino-5,6-dichloro-3H-isoindol-1-ylamine,
5,6-bis(ethoxymethyl)-3-imino-3H-isoindol-1-ylamine,
3-amino-1-imino-1H-isoindole-4,7-diol,
4,7-dichloro-3-imino-3H-isoindol-1-ylamine,
4,5,7-trichloro-3-imino-N6,N6-dimethyl-3H-isoindole-1,6-diamine,
4,5,6,7-tetrachloro-3-imino-3H-isoindol-1-ylamine,
4,5,6,7-tetrafluoro-3-imino-3H-isoindol-1-ylamine,
2-(3-aminoisoindol-1-ylideneamino)ethanol,
3-(3-aminoisoindol-1-ylideneamino)-3-methylpentane-1,5-diol,
N-(3-aminoisoindol-1-ylidene)guanidine,
7-imino-7H-pyrrolo{3,4-b}pyrid-5-ylamine,
7-imino-7H-pyrrolo{3,4-b}pyrazin-5-ylamine,
7-imino-2,3-dimethyl-7H-pyrrolo{3,4-b}pyrazin-5-ylamine,
7-imino-7H{1,4}dithiino{2,3-c}pyrrol-5-ylamine,
7-imino-2,3-dimethyl-7H-{1,4}dithiino{2,3-c}pyrrol-5-ylamine,
7-imino-2,3-dihydro-7H-{1,4}dithiino{2,3-c}pyrrol-5-ylamine,
7-imino-2-methyl-2,3-dihydro-7H-{1,4}dithiino{2,3-c}pyrrol-5-ylamine,
3-aminoisoindol-1-one,
3-amino-7-methylisoindol-1-one,
3-amino-7-hydroxymethylisoindol-1-one,
3-amino-7-chloroisoindol-1-one,
3-amino-4-chloroisoindol-1-one,
3-amino-1-oxo-1H-isoindole-4-sulphonic acid,
3-amino-4-nitroisoindol-1-one,
3-amino-6-nitroisoindol-1-one,
3-amino-6-methylisoindol-1-one,
3-amino-6-chloroisoindol-1-one,
3-amino-6-bromoisoindol-1-one,
3-amino-6-methylsulphanylisoindol-1-one,
3-amino-6-methoxyisoindol-1-one,
3-amino-5-chloroisoindol-1-one,
3-amino-5-fluoroisoindol-1-one,
3-amino-5-methoxyisoindol-1-one,
3-amino-5-nitroisoindol-1-one,
ethyl 3-amino-1-oxo-1H-isoindole-5-carboxylate,
3-amino-5,6-dichloroisoindol-1-one,
3-amino-5,6-dibromoisoindol-1-one,
3-amino-4,7-dichloroisoindol-1-one,
3-amino-4,5,7-trichloroisoindol-1-one,
3-amino-4,5,6,7-tetrachloroisoindol-1-one,
3-amino-4,5,7-trichloro-6-methylsulphanylisoindol-1-one,
3-amino-4,5,6,7-tetrabromoisoindol-1-one,
3-amino-4,5,6,7-tetrafluoroisoindol-1-one,
3-methylaminoisoindol-1-one,
3-ethylaminoisoindol-1-one,
3-propylaminoisoindol-1-one,
3-dimethylaminoisoindol-1-one,
7-ethylaminopyrrolo{3,4-b}pyrid-5-one,
7-aminopyrrolo{3,4-b}pyrid-5-one,
3-aminopyrrolo{3,4-c}pyrid-5-one,
3-amino-6-methylpyrrolo{3,4-c}pyrid-5-one,
5-aminopyrrolo{3,4-b}pyrid-7-one,
7-aminopyrrolo{3,4-b}pyrazin-5-one,
7-amino-2-methylpyrrolo{3,4-b}pyrazin-5-one,
7-amino-2,3-dimethylpyrrolo{3,4-b}pyrazin-5-one,
7-amino-2,3-dihydro-{1,4}dithiinopyrrol-5-one,
3-imino-2-methyl-2,3-dihydroisoindol-1-one,
3-imino-2-ethyl-2,3-dihydroisoindol-1-one,
3-imino-2-propyl-2,3-dihydroisoindol-1-one,
2-hydroxymethyl-3-imino-2-methyl-2,3-dihydroisoindol-1-one,
2-(2-hydroxyethyl)-3-imino-2-methyl-2,3-dihydroisoindol-1-one,
2-(1-imino-3-oxo-1,3-dihydroisoindol-2-yl)ethanesulphonic acid,
3-(imino-3-oxo-1,3-dihydroisoindol-2-yl)propionic acid,
2-(3-hydroxypropyl)-3-imino-2,3-dihydroisoindol-1-one,
5-imino-6-methyl-5,6-dihydropyrrolo{3,4-b}pyrid-7-one,
or a cosmetically acceptable salt thereof.

5. A method according to claim 1, wherein said compound of formula (I) functions as an oxidizing-agent-free dye precursor.

6. A method according to claim 5, wherein said compound of formula (I) is combined with a compound containing a primary or secondary amine function.

7. A method for the preparation of a composition for dyeing a keratin fiber, said method comprising:
   forming a composition comprising at least one compound containing a primary or secondary amine function; and a compound of formula (I) or a cosmetically acceptable salt thereof, as an oxidizing-agent-free dye precursor:

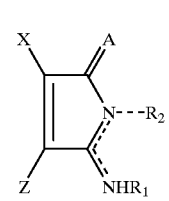

(I)

in which
   $R_1$ and $R_2$, which are the same or different, denote hydrogen, alkyl, hydroxyalkyl, polyhydroxyalkyl, alkylhydroxyalkyl, aminoalkyl, alkylaminoalkyl, (dihydroxy)alkylaminoalkyl, or -alkyl-NR'R" wherein R' and R" are alkyl or form, together with the nitrogen atom to which they are attached, a 5- or 6- membered aliphatic or heterocyclic ring;
   wherein all the alkyl groups of $R_1$, $R_2$, R' and R" contain from 1 to 4 carbon atoms and are linear or branched, and further wherein $R_2$ optionally is not present,
   A denotes O or NH;

X and Z together form a saturated or unsaturated, aromatic or heterocyclic, 5- or 6-membered hydrocarbon ring which is optionally interrupted by one or more nitrogen or sulphur atoms, and which is optionally substituted with one or more groups comprising $NO_2$, $NH_2$, acetylamino, OH, $SO_3H$, F, Cl, Br, $CH_3SO_2$, $-CF_3$, $-OCF_3$, $(C_1-C_4)$alkyl, $(C_1-C_4)$alkoxy, $(C_1-C_4)$alkylthio, and $(C_1-C_4)$alkoxycarbonyl, with the proviso that when X and Z together form a benzene ring, A is O when $R_2$ is not present and $R_1$ denotes hydrogen, $C_1-C_4$-alkyl, hydroxy-$C_1-C_4$-alkyl, or polyhydroxy-$C_1-C_4$-alkyl.

8. A composition for dyeing a keratin fiber comprising at least one compound containing a primary or secondary amine function; and as an oxidizing-agent-free dye precursor, at least one compound of formula (I) or a cosmetically acceptable salt thereof:

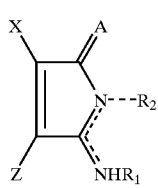

(I)

in which $R_1$ and $R_2$, which are the same or different, denote hydrogen, alkyl, hydroxyalky, polyhydroxyalkyl, alkylhydroxyalkyl, aminoalkyl, alkylaminoalkyl, (dihydroxy)alkylaminoalkyl, or -alkyl-NR'R'' wherein R' and R'' are alkyl or form, together with the nitrogen atom to which they are attached, a 5- or 6- membered aliphatic or heterocyclic ring;

wherein all the alkyl groups of $R_1$, $R_2$, R' and R'' contain from 1 to 4 carbon atoms and are linear or branched, and further wherein $R_2$ optionally is not present, A denotes O or NH;

X and Z together form a saturated or unsaturated, aromatic or heterocyclic, 5- or 6-membered hydrocarbon ring which is optionally interrupted by one or more nitrogen or sulphur atoms, and which is optionally substituted with one or more groups comprising $NO_2$, $NH_2$, acetylamino, OH, $SO_3H$, F, Cl, Br, $CH_3SO_2$, $-CF_3$, $-OCF_3$, $(C_1-C_4)$alkyl, $(C_1-C_4)$alkoxy, $(C_1-C_4)$alkylthio, and $(C_1-C_4)$alkoxycarbonyl, with the proviso that when X and Z together form a benzene ring, A is O when $R_2$ is not present and $R_1$ denotes hydrogen, $C_1-C_4$-alkyl, hydroxy-$C_1-C_4$-alkyl, or polyhydroxy-$C_1-C_4$-alkyl, in a medium suitable for dyeing.

9. A composition according to claim 8, wherein said keratin fibre is human hair.

10. A composition according to claim 8, wherein said at least one compound containing a primary or secondary amine function is an aromatic compound, a heterocyclic compound, an amino acid or an oligopeptide containing from 2 to 9 amino acids.

11. A composition according to claim 8, wherein said composition has a pH ranging from 2 to 11.

12. A composition according to claim 8, wherein said at least one compound of formula (I) is present in a concentration ranging from 0.01 to 5% by weight, relative to the total weight of the composition.

13. A composition according to claim 8, wherein said at least one compound containing a primary or secondary amine function is present in a concentration ranging from 0.01 to 5% by weight, relative to the total weight of the composition.

14. A composition according to claim 13, wherein said at least one compound containing a primary or secondary amine function is present in a concentration ranging from 0.15 to 2% by weight, relative to the total weight of the composition.

15. A composition according to claim 8, wherein said medium suitable for dyeing is an aqueous medium comprising water and/or at least one organic solvent.

16. A composition according to claim 15, wherein said at least one organic solvent is selected from alcohols, glycols and glycol ethers.

17. A composition according to claim 16, wherein said at least one organic solvent is present in a proportion ranging from 0.5 to 20% by weight relative to the total weight of the composition.

18. A composition according to claim 17, wherein said at least one organic solvent is present in a proportion ranging from 2 to 10% by weight relative to the total weight of the composition.

19. A composition according to claim 8, wherein said composition further comprises at least one fatty amide.

20. A composition according to claim 8, wherein said composition is in the form of a liquid, a cream, a gel or an aerosol.

21. A composition according to claim 8 comprising, in a medium suitable for dyeing, (A) at least one compound of formula (I) or a cosmetically acceptable salt thereof, and (B) at least one compound containing a primary or secondary amine function; wherein component (A) and component (B) are stored separately and either (i) mixed together, at the time of use, for application to a keratin fiber, or (ii) applied sequentially to a keratin fiber.

22. A process for dyeing a keratin fiber comprising:

applying the composition according to claim 8 to a wet or dry keratin fiber, leaving the composition on said keratin fiber for an amount of time effective for said composition to act on said keratin fiber, rinsing said keratin fiber, optionally washing said keratin fiber, rinsing said keratin fiber again, and drying said keratin fiber.

23. A process according to claim 22, wherein said keratin fibre is human hair.

24. A process according to claim 22, wherein said composition is left on said keratin fiber for approximately 3 to approximately 60 minutes.

25. A process according to claim 24, wherein said composition is left on said keratin fiber for approximately 5 to approximately 45 minutes.

26. A process for dyeing a keratin fiber comprising: applying to a wet or dry keratin fiber the composition of claim 8.

27. A multi-compartment kit, for dyeing a keratin fiber comprising at least two compartments, (A) and (B);

wherein (A) includes, in a medium suitable for dyeing, at least one compound of formula (I) or a cosmetically acceptable salt thereof:

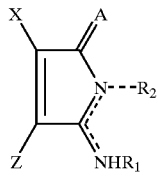
(I)

in which

R$_1$ and R$_2$, which are the same or different, denote hydrogen, alkyl, hydroxyalkyl, polyhydroxyalkyl, alkylhydroxyalkyl, aminoalkyl, alkylaminoalkyl, (dihydroxy)alkylaminoalkyl, or -alkyl-NR'R" wherein R' and R" are alkyl or form, together with the nitrogen atom to which they are attached, a 5- or 6- membered aliphatic or heterocyclic ring;

wherein all the alkyl groups of R$_1$, R$_2$, R' and R" contain from 1 to 4 carbon atoms and are linear or branched, and further wherein R$_2$ optionally is not present, A denotes O or NH;

X and Z together form a saturated or unsaturated, aromatic or heterocyclic, 5- or 6-membered hydrocarbon ring which is optionally interrupted by one or more nitrogen or sulphur atoms, and which is optionally substituted with one or more groups comprising NO$_2$, NH$_2$, acetylamino, OH, SO$_3$H, F, Cl, Br, CH$_3$SO$_2$, —CF$_3$, —OCF$_3$, (C$_1$–C$_4$)alkyl, (C$_1$–C$_4$)alkoxy, (C$_1$–C$_4$)alkylthio, and (C$_1$–C$_4$)alkoxycarbonyl, with the proviso that when X and Z together form a benzene ring, A is O when R$_2$ is not present and R$_1$ denotes hydrogen, C$_1$–C$_4$-alkyl, hydroxy-C$_1$–C$_4$-alkyl, or polyhydroxy-C$_1$–C$_4$-alkyl, and wherein (B) includes, in a medium suitable for dyeing, at least one compound containing a primary or secondary amine function.

* * * * *